United States Patent
Karlsson

(10) Patent No.: US 6,210,390 B1
(45) Date of Patent: Apr. 3, 2001

(54) FASTENING ARRANGEMENT FOR ABSORBENT GARMENTS

(75) Inventor: Katharina Karlsson, Hovås (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/331,843

(22) PCT Filed: Dec. 17, 1997

(86) PCT No.: PCT/SE97/02136

§ 371 Date: Jul. 23, 1999

§ 102(e) Date: Jul. 23, 1999

(87) PCT Pub. No.: WO98/29081

PCT Pub. Date: Jul. 9, 1998

(30) Foreign Application Priority Data

Dec. 27, 1996 (SE) .................................................. 9604804

(51) Int. Cl.[7] .................................................... A61F 13/15
(52) U.S. Cl. ........................ 604/391; 604/390; 604/392; 604/394; 604/396
(58) Field of Search ................................. 604/391, 392, 604/393, 394, 390, 396

(56) References Cited

U.S. PATENT DOCUMENTS 4,964,860 * 10/1990 Gipson et al. ..................... 604/391
5,611,789 * 3/1997 Seth ..................................... 604/391
5,906,604 * 5/1999 Ronnberg et al. .................... 604/386

\* cited by examiner

Primary Examiner—John G. Weiss
Assistant Examiner—Michele Kidwell
(74) Attorney, Agent, or Firm—Young & Thompson

(57) ABSTRACT

An absorbent garment such as an incontinence diaper includes a belt and an absorption unit, the rear short side of which is preferably releasably joined with the belt. The opposite short side of the absorption unit, situated at the front of a user, has two end parts, each situated at one end of the short side, which each by their hook and loop fasteners are releasably connectable with the waist belt in a plurality of positions in relation thereto. Each fastener has a piece of first hook and loop material non-releasably connected with one of the casing layers within the respective end parts, and a therewith cooperating piece of second, complementary hook and loop material which on its side facing away from the hook and loop devices is provided with an adhesive layer which in the unused state of the fasteners is covered by a protective layer. The protective layer is suitably fastened to the inner casing layer on the end part of the front short side, whereby a garment with clean contours is obtained and loose pieces of protective layer avoided when the absorption unit is brought into use the first time.

Figure 1:
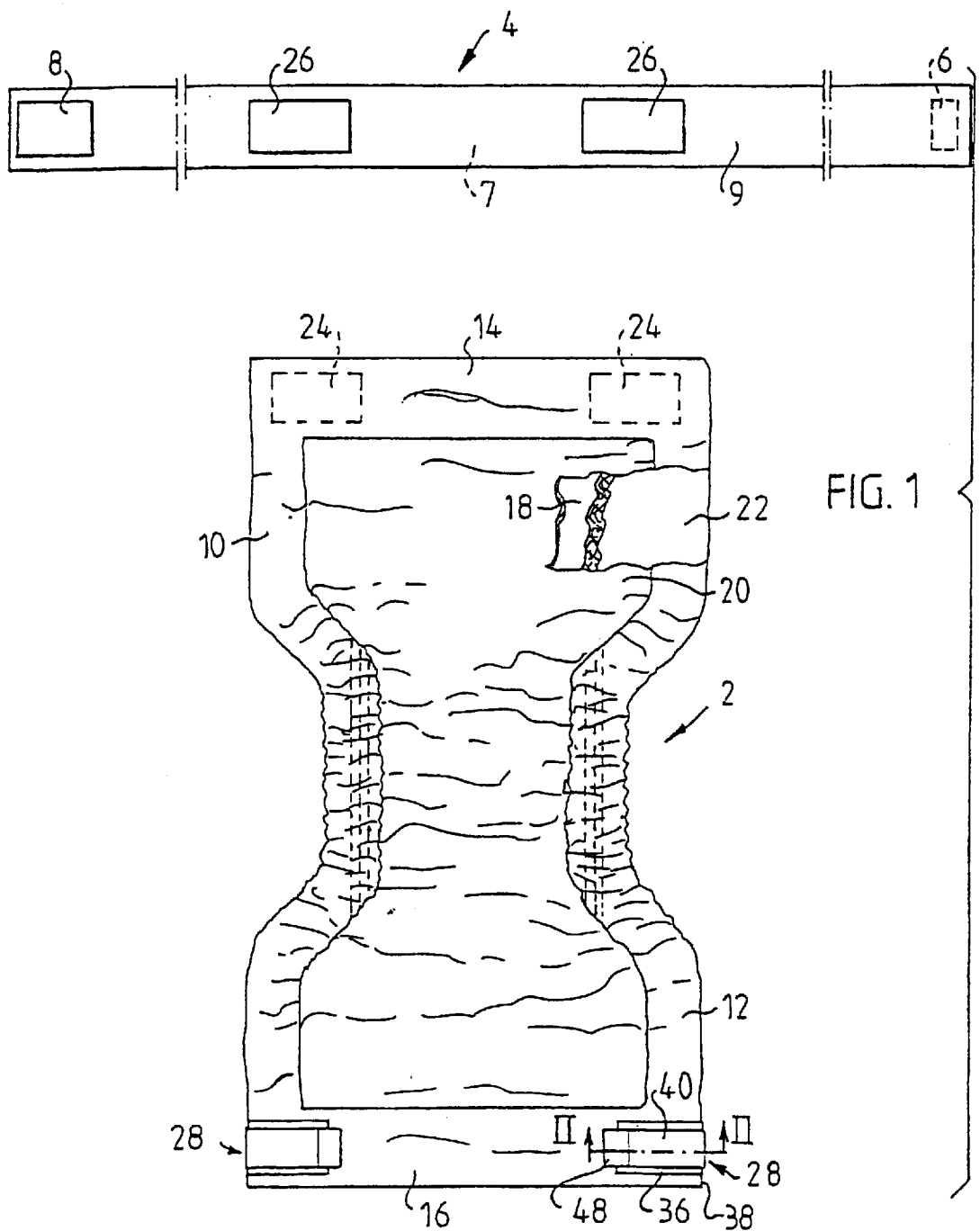

8 Claims, 2 Drawing Sheets

FASTENING ARRANGEMENT FOR ABSORBENT GARMENTS

FIELD OF THE INVENTION

The present invention relates to absorbent garments, especially incontinence protectors, according to the preamble to the appended claim 1.

BACKGROUND

An absorbent garment of the above mentioned type is described in the Swedish Patent Application 9301631-9 and shows fixed tapes of hook material for hook and loop joints on the absorption unit, also known as a chassis. These are intended to cooperate with the outside of the belt. For this purpose the outside of the belt is made as a unit from a complementary hook and loop material suitable for cooperation with the hook material—a loop material. The belt is made as a multilayer laminate.

In order for the fastening means to be able to hold up a large, fluid-drenched absorption unit by the belt, a hook and loop material with a relatively high force transmitting ability is required. Such materials are expensive, wherefore the belt becomes expensive. This is unfavourable, especially if the belt is intended for single use or is fastened to a garment of single use-type.

A similar fastening between an absorption unit and a belt is shown in EP-A-0 409 307, where the belt is intended to be able to be used a number of times.

Additionally, GB 2 257 895 describes a hook and loop fastening arrangement in another type of product, viz. an hourglass-shaped diaper or incontinence protector without a belt. In each end part of the rear waistband is fastened a projecting tape, which supports a hook and loop fastening means. This has two hook and loop tapes which grip each other and an outwardly facing layer of glue which during the first use of the diaper is fastened on the front waistband. The joint can thereafter be opened and closed by the hook and loop tapes being pulled apart and pressed together again.

A motive for the invention is the task of providing an absorbent garment of the type mentioned in the introduction, especially for single use, which is cheaper than known such garments. It should, however, still be possible to comfortably adapt the garment to the shape of the body of the user by the selection of different connecting positions between the absorption unit and the belt.

SUMMARY OF THE INVENTION

According to the invention this task is fulfilled through the garment having the characteristics mentioned below.

As the belt material itself does not need to interact with the first hook and loop material, which appropriately is a hook material, it can be made of a cheap and pliable material, e.g. a thin nonwoven textile material, nonwoven, a plastic film coated or laminated with an outer material which is kind to the skin, or even a purely plastic film. The exposed glue layer on the fastening means can be fastened in arbitrarily desired places on the belt the first time the garment is used, whereby an optimal fitting of the garment to the user is achieved. The absorption unit can thereafter be detached and refastened to the belt through the hook and loop joints being opened and then pushed together again. If the two pieces of complementary hook and loop material then are again positioned directly in front of each other, the earlier made fitting of the garment is again achieved but a certain adjustment is also possible.

An advantageous design for packing without projecting tapes or ends of bands is obtained by the protective layer being fastened to the inner casing layer on the end part of the front short side. The fastening means in the unused condition then is fastened to the front short side and can be removed and folded out when the short side is to be fastened to the belt for the first time. As the protective layer is attached to the absorption unit, the user does not have to take care of loose protective layer pieces when the garment is to be put on.

Further advantages and characteristics of the invention are evident from the independent claims and from the following description of embodiments with reference to the accompanying figures.

FIGURES

Figure 2:
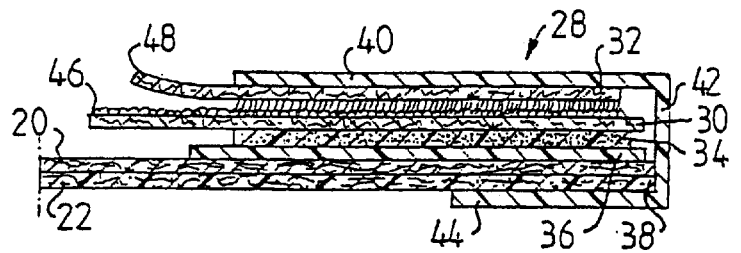
Figure 3:
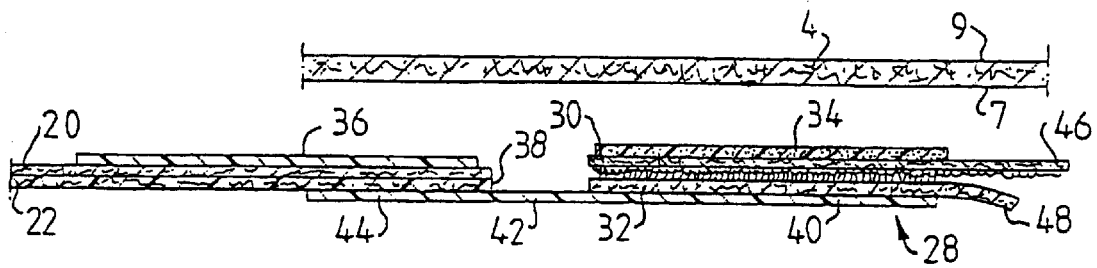
Figure 4:
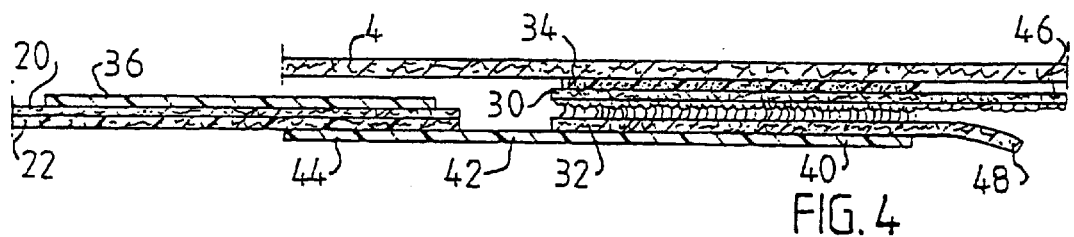
Figure 5:
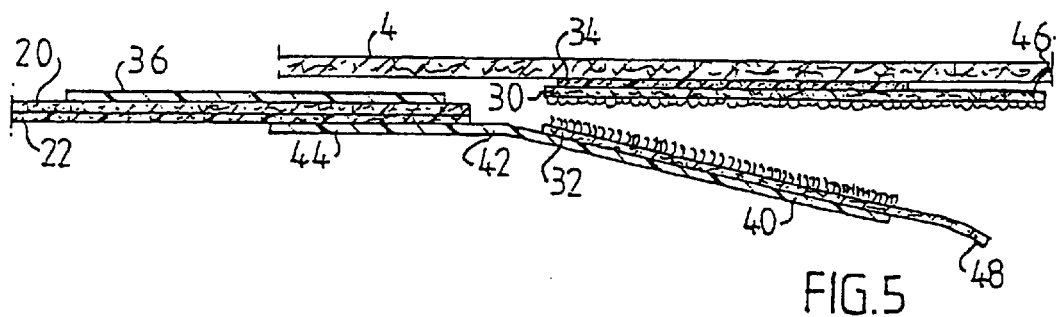

The figures show:

FIG. 1, a preferred embodiment of an absorbent garment according to the invention in the shape of an incontinence diaper, seen from the side facing towards the user during the use and partially cut away, FIG. 2, a section through a part of a diaper with fastening means attached thereto, seen from the line II—II in FIG. 1 and with the fastening means in the unused state, and FIGS. 3, 4 and 5, sections similar to FIG. 2 with the fastening means in different states of use.

DETAILED DESCRIPTION OF THE EMBODIMENTS

FIG. 1 shows an absorbent garment according to the invention in the shape of an incontinence diaper, which consists of an absorption unit 2, also called chassis, and a separate belt 4 intended to releasably support the absorption unit 2. The belt 4 is made of a band of thin nonwoven textile material nonwoven, and has at its ends tapes 6,8 of complementary hook and loop material for fastening together the belt around the waist of a user. For example, the tape 6 can be formed of so-called hook material and be fixed to the side 7 of the belt 4 facing away from user during the use, while the tape 8 projecting in the longitudinal direction of the belt is made of so-called loop material and is fixed to the side 9 of the belt facing towards the user.

The absorption unit 2 has two long sides 10,12 and two short sides 14,16. The short side 14 is intended during use to be bent towards the rear of the user and the short side 16 bent forwards. The absorption unit 2 is built up of a central body of absorption material 18, which is contained between an inner casing layer 20 of liquid-permeable material, e.g. nonwoven, and an outer casing layer 22 of liquid-tight material, e.g. plastic film.

The rear short side is provided with two tapes 24 of a hook and loop hook material, spaced apart a distance and rigidly attached to the outer casing layer 22. The belt 4 is provided on its side facing toward the user with two tapes 26 of a hook and loop hook material arranged spaced apart essentially the same distance. When the belt 4 is brought around the waist of the user, the hook material tape 6 at one end of the belt is fastened to the loop material tape 8 at the other end of the belt. The tape 8 has such a length that adaptation to the waist size of the user is permitted. The absorption unit 2 is fastened by the belt 4 through the hook material tapes 24 on its rear short side 14 being pressed against the loop material tapes 26 on the belt. This can be performed either before or after the belt has been fastened around the waist. When the belt 4 is fastened around the waist of the user and the absorption unit 2 is fastened to the belt and hangs down behind the user, the front short side 16 of the absorption unit is moved between the user's legs and up over the abdomen to be fastened to the belt 4. The fastening takes place with the help of two fastening means 28 which are each firmly joined with one end of the short side 16 and which is described more closely below with the help of FIGS. 2–5.

FIG. 2 shows a section through the right end seen in FIG. 1 of the front short side 16 of the absorption unit 2 and the thereupon attached fastening means 28, which comprises a number of layers of different materials. The refastenable fastening device of the fastening means 28 consists of first and second complementary tapes 30,32 of hook and loop material which grip each other, as shown in FIG. 2. The first tape 30, which can be made of loop material, is provided with a layer 34 of a powerful adhesive on its side facing away from the hook and loop means. The adhesive layer lies in contact with a first plastic tape 36 which is fixed, e.g. glued, on the inner casing layer 20 of the absorption unit 2 next to the end edge 38 of the front short side 16. The surface of the first plastic tape 36 which is facing towards the first tape 30 of loop material is smooth or treated with release means and forms a so-called release surface so that the adhesive layer 34 can easily be removed therefrom. One end 40 of a second plastic tape 42 is fastened to the second tape 32 on the side facing away from the hook and loop means, shown in the example as hook means. The second plastic tape 42 extends around the end edge 38 of the short side 16 and has its other end 44 fastened onto the outer casing layer 22 on the outside of the short side 16. The end 46 of the first tape 30 facing away from the end edge 38 extends further from the end edge 38 than the adhesive layer 34 and forms a gripping tab. The second tape 32 has essentially the same size as the first tape 30 and its end 48 lying directly in front of the end 46 of the first tape 30 lacks hook and loop means, shown in the example as hooks, whereby the end forms a gripping tab.

FIG. 2 shows the fastening means 28 in the state it has when it is still unused. When the belt 4 of the absorbent garment is fastened around the waist of the user and the absorption unit 2 is drawn up over the stomach of the user, the front short side 16 is fastened to the outside 7 of the belt 4. One then grips with the fingers one or both of the gripping tabs 46,48 and draws the fastening means 28 upwards from the inner casing layer 20 of the short side 16. The adhesive layer 34 then comes off the first plastic tape 36. With the second plastic tape 42 as a hinge the first and second tapes 30,32 with appended adhesive layer 34 can be folded out to a position where they form a continuation of the short side 16. This position is shown in FIG. 3) which also shows a part of the belt 4. With the fingers sill gripping around one or both of the tabs 46,48, the adhesive layer 34 on the fastening means 28 is pressed against the outside 7 of the belt 4. A good connection between the adhesive layer 34 and the outside 7 of the belt 4 is obtained by pressing the outer end 40 of the second plastic tape 42, whereby the belt 4 is supported by the user's abdomen or side. The fastening means 28 now takes up the state shown in FIG. 4. The first tape 30 now is fixed onto the belt 4 and forms a receiving zone, a so-called target, intended for cooperation with the second tape 32.

If for some reason one wishes to remove the absorption unit 2 from the belt 4, one grips the gripping tab 48 on the second tape 32 and draws it away from the first tape 30, see FIG. 5. It is important that the strength of the adhesive joint between the adhesive layer 34 and the outside 7 of the belt 4 and the first tape 30, respectively, is so adapted in relation to the strength of the joint formed by the first and second tapes that the joint opens before the adhesive layer comes off from the belt or first tape 30.

When the absorption unit 2 is released from the belt 4 according to FIG. 5, it is easy to refasten it to the belt by pressing together the first and second tapes 30 and 32.

The invention is not limited to the embodiment described above and shown in the drawing. For example, the first tape 30 can alternatively be of hook material and the second tape 32 of loop material. The fastening means 24/26 between the belt 4 and the absorption unit 2 can alternatively be an adhesive joint, or the belt 4 can be permanently connected to the absorption unit 2, e.g. by welding by the rear short side 14.

What is claimed is:

1. Absorbent garment, especially incontinence protector, comprising:

an absorption unit (2) having a first casing layer (20) which is liquid-permeable, a second casing layer (22) which is liquid-tight, and an absorption body (18) situated between the first and second casing layers, the absorption unit (2) having a front and a rear short side (16, 14);

a waist belt (4) for fastening around the waist of a user, which is joined or connectable with the rear short side (14) of the absorption unit (2);

the front short side (16) having two end parts, each end part situated at one end of the front short side, and each end part having hook and loop fastening means (28) for releasably connecting said end part with the waist belt (4) in a plurality of positions in relation thereto;

each hook and loop fastening means (28) having a piece (32) of a first hook and loop material non-releasably joined with one of the first and second casing layers within the respective end parts, and a therewith cooperating piece (30) of second, complementary hook and loop material, which on its side facing away from the hook and loop means is provided with an adhesive layer (34);

the adhesive layer (34) in an unused state of the fastening means (28) being covered by a protective layer (36);

the protective layer (36) being fixed to the first casing layer (20) at the end part of the front short side (16); and a surface of the waist belt (4) intended for cooperation with the fastening means (28) being formed of a material which lacks the ability to cooperate, by gripping, with the first hook and loop material (32) to a sufficient degree when the garment is used.

2. Garment according to claim 1, characterized in that the first hook and loop material (32) is a hook material and that the second hook and loop material (30) is a loop material.

3. Garment according to claim 1, characterized in that the waist belt (4) is unreleasably connected with the absorption unit (2) at its rear short side (14).

4. Garment according to claim 1, characterized in that the absorption unit (2) is releasably connectable (24/26) with the waist belt (4).

5. Garment according to claim 4, characterized in that the absorption unit (2) is releasably connectable with the waist belt (4) by means of hook and loop fastening means (24, 26).

6. Garment according claim 2, characterized in that the waist belt (4) is unreleasably connected with the absorption unit (2) at its rear short side (14).

7. Garment according claim 2, characterized in that the absorption unit (2) is releasably connectable (24, 26) with the waist belt (4).

8. Garment according to claim 7, characterized in that the absorption unit (2) is releasably connectable with the waist belt (4) by means of hook and loop fastening means (24,26).

* * * * *